United States Patent [19]

Ray et al.

[11] Patent Number: 4,772,287
[45] Date of Patent: Sep. 20, 1988

[54] PROSTHETIC DISC AND METHOD OF IMPLANTING

[75] Inventors: Charles D. Ray, Deephaven; Terry P. Corbin, Golden Valley, both of Minn.

[73] Assignee: CeDaR Surgical, Inc., Minnetonka, Minn.

[21] Appl. No.: 87,424

[22] Filed: Aug. 20, 1987

[51] Int. Cl.$^4$ .............................................. A61F 1/24
[52] U.S. Cl. ........................................ 623/17; 128/69; 128/92 YM; 128/DIG. 20
[58] Field of Search ............... 623/10, 12, 16, 17; 128/92 R, 92 YM, DIG. 20, 69

[56] References Cited

U.S. PATENT DOCUMENTS

| | | | |
|---|---|---|---|
| 3,426,364 | 2/1969 | Lumb | 623/17 |
| 3,867,728 | 2/1975 | Stubstad et al. | 623/17 |
| 3,875,595 | 4/1975 | Froning | 623/17 |
| 4,309,777 | 1/1982 | Patil | 623/17 |
| 4,349,921 | 9/1982 | Kuntz | 623/17 |
| 4,554,914 | 11/1985 | Kapp et al. | 623/17 X |
| 4,636,217 | 1/1987 | Ogilvie et al. | 623/17 |
| 4,643,734 | 2/1987 | Lin | 623/16 |
| 4,655,777 | 4/1987 | Dunn et al. | 623/17 X |
| 4,685,447 | 8/1987 | Iverson et al. | 128/DIG. 20 X |

FOREIGN PATENT DOCUMENTS

| | | | |
|---|---|---|---|
| 1015989 | 10/1952 | France | 128/69 |
| 0895433 | 1/1982 | U.S.S.R. | 623/17 |

OTHER PUBLICATIONS

A Bulletin entitled "Cab-O-Sil Properties and Functions" from Cabot Corp., 9-1983, p. 10.

Primary Examiner—Richard J. Apley
Assistant Examiner—David J. Bender
Attorney, Agent, or Firm—Moore & Hansen

[57] ABSTRACT

By implanting two prosthetic disc capsules side-by-side into a damaged disc of a human spine, both height and motion, including front-to-back bending, can be maintained. The prosthetic disc capsules have an outer layer of strong, inert fibers intermingled with a bioresorbable material which attracts tissue ingrowth, a bladder enveloped by the layer, and a thixotropic gel filling the bladder. The prosthetic disc capsules can be surgically implanted by (1) jacking apart the vertebrae adjacent a damaged disc, (2) forming a substantially sagital bore in the damaged disc near each of its lateral edges, and (3) inserting one of the capsules axially into each bore.

16 Claims, 2 Drawing Sheets

PROSTHETIC DISC AND METHOD OF IMPLANTING

BACKGROUND ART

1. Field of the Invention

The invention concerns prosthetic discs and a simple surgical procedure for implanting a pair of prosthetic disc capsules to repair a degenerated disc of the spine of a vertebrate, especially the spine of a human being.

2. Description of Related Art

The normal intervertebral disc has an outer ligamentous ring called the anulus which binds the adjacent vertebrae together and is constituted of collagen fibers that are attached to the vertebrae and cross each other so that half of the individual fibers will tighten as the vertebrae are rotated in either direction, thus resisting twisting or torsional motion. Torsional movement between vertebral segments is further restricted by the facet joints.

Deep inside the anulus lies a nucleus pulposis of loose tissue which is slippery and slimy (having about 85% water content) and moves about during bending from front to back or from side to side. Thus, as the opposing surfaces of the vertebrae alter their parallel relationship to each other with bending, the nuclear tissue moves about to fill up the change in distance (wedging) that occurs in the opposing ends of the disc space. With bending, the anulus will bulge on the downward wedged side and be stretched tightly on the upward wedged side.

A classical disc herniation occurs when the anular fibers are weakened or torn and the inner tissue of the nucleus becomes permanently bulged, distended, or extruded out of its normal anular confines. Leg pain in such cases results from this nuclear tissue (or an intact, weakened, bulging anulus) compressing a nerve which passes outward from the spinal canal to the leg.

A major cause of persistent, disabling back pain takes place when the anulus becomes chronically inflamed by a degenerative process. Small nerves that come from branches encircling the outside of the anulus penetrate for a short distance (perhaps 6 to 8 mm) into the anular fibers. constant abnormal motion between the fiber layers of the anulus, due to loss of bonding between them, may stretch and grind the tiny pain fiber nerve endings. Thus the patient becomes sensitive to the slightest movement. These cases require some form of mechanical limitation to intervertebral disc motion at the painful segment. For the most persistent cases, bony fusions are often performed to stop the painful motion by permanently locking the vertebrae together. In many cases it may be preferred to allow some minor movement (less than that which causes the pain). Preserving some movement helps to prevent mechanical breakdown at nearby segments. At present, to attempt to make and maintain these flexible fusions is not reliably feasible.

Whenever the nuclear tissue is herniated or removed by surgery, the disc space will narrow and lose much of its mobility. Considering that rotation is potentially destructive to the anulus and nucleus, rotation should be limited by any prosthetic device to replace the removed, herniated or degenerated disc, preferably while allowing bending, especially forward and backward. Lateral bending is of lesser importance.

Although we are not aware of any means currently being used to preserve both the height of the disc space and important motions of the vertebral segment, a number of patents describe prosthetic discs that are said to be useful for those purposes. For example, U.S. Pat. No. 3,875,595 (Froning) shows a prosthesis shaped to replace the entire nucleus pulposis of an intervertebral disc. Froning's "prosthesis is a hollow, flexible bladder-like member which is filled with a fluid and/or plastic under adjustable pressure. The pressure may be increased or decreased while the prosthesis is in place over a period of time to determine by trial and error the optimum pressure, and thereupon the stem of the prosthesis is removed. The optimum pressure is maintained over an indefinite period of time by providing an inflating fluid or plastic having properties for holding fluid or water under pressure normally occurring within the disc sufficient to avoid depletion of the inflating contents, a feature which would duplicate the feature of the normal disc" (col. 1, lines 30-43). Froning's prosthesis has stud-like protrusions which fit into sockets that have been forced through the bony end plates of the adjacent vertebrae to anchor the prosthesis against slippage.

U.S. Pat. No. 4,349,921 (Kuntz) shows an intervertebral disc prosthesis formed from any biologically acceptable material such as high density polyethylene, polymethacrylate, stainless steel, or chrome cobalt alloy and dimensionally shaped to replace a natural disc. One of the longitudinal ends of the prosthesis can have a raised flange to facilitate handling and to prevent penetration to an excessive depth, while the other longitudinal end is wedge-shaped to facilitate insertion. The superior and inferior faces are provided with surface characteristics such as grooves, corrugations, or projections to produce a "friction-fit" and are convex to correspond to the adjacent vertebral surfaces.

U.S. Pat. No. 3,867,728 (Stubstad et al.) shows intervertebral disc prostheses of a variety of constructions. Each of these prostheses has a core made of elastic polymer, e.g., a reinforced resilient block of elastomer such as silicone rubber or polyurethane, and a covering providing an outer surface of an open-pore tissue-ingrowth-receptive material. While most of the illustrated prostheses are single elements of a shape approximating that of a human disc, "another version includes a plurality of flexible, curved, bar-like elements with configurations which allow them to lie side by side so as to occupy the interior space of a natural disc from which the nucleus pulposus has been removed" (penultimate sentence of Abstract). See FIGS. 23 and 24. To repair a ruptured disc with either a single or a multi-element prosthesis, the interlaminar space is posteriorly exposed and "laminectomy is performed to gain better access to the disc space and to provide an opening . . . through which the nucleus pulposus will be removed and the prosthesis inserted. The spinal dura and nerve root are identified, the root is dissected free, and together these are retracted laterally to expose the herniation" (col. 14, lines 17-27). After cleaning out the ruptured disc to create a space to receive the prosthesis, "the end plate that will be adjacent to the ingrowth surface of the prosthesis is scraped clean of loose tissue and left with a bleeding surface to promote fixation of the prosthesis by tissue ingrowth" (col. 14, lines 35-39). If the two-element prosthesis is used, "The two segments may be further stabilized by tying them together by cords 129 or by suturing to one of the adjacent vertebrae or other available tissue" (col. 14, lines 48-50).

Intervertebral disc prostheses which are mechanically fastened between vertebrae are shown in U.S. Pat. No. 4,554,914 (Kapp et al.); U.S. Pat. No. 4,309,777 (Patil); U.S. Pat. No. 3,426,364 (Lumb); and U.S. Pat. No. 4,636,217 (Ogilvie et al.).

SUMMARY OF THE INVENTION

The invention provides an elongated, cylindrical prosthetic disc capsule having a diameter approximating the height of a human disc space and a length approaching the sagittal diameter of the vertebral body. Its outer layer is made of strong, inert fibers intermingled with a bioresorbable (or bioabsorbable) material which attracts tissue ingrowth and surrounds a bladder. The fluid preferably is a thixotropic gel having a viscosity and velocity-shear behavior imitating the natural rheology of intradiscal nuclear tissue.

The prosthetic disc capsules should be implanted in pairs. A surgical procedure for their implantation includes the steps of (1) jacking apart the vertebrae adjacent to a damaged disc, (2) forming a substantially sagittal bore in the damaged disc near each of its lateral edges and spaced from the other bore, and (3) inserting an elongated cylindrical prosthetic disc capsule axially into each bore. When two of these capsules have been inserted side-by-side into the nucleus of the anulus of a damaged disc, each lying near one of the lateral edges of the disc, they will maintain both height and motion, including front-to-back bending, at the disc space, but will limit rotation, translocation and, to a lesser degree, bending from side to side.

The preferred posterior surgical approach involves drilling an 11-mm hole to provide a window through each of the facet joints, either before or after step (1) of the above-outlined surgical procedure. Then using the windows for access, the surgeon performs step (2) of the procedure and removes debris from the boring and any other unwanted material of the nucleus of the damaged disc. Then in step (3), a prosthetic disc capsule is inserted through each of the windows into the bore. In some cases, the implanted disc capsules can reestablish disc height, an especially desirable objective in massively herniated discs or those that have continued to shrink following a much earlier herniation.

The bores drilled in the disc preferably are sufficiently large to slightly decorticate the end plates of the adjacent vertebrae, thus promoting the attachment of the prosthetic capsules to the bone and adjacent tissue.

In the foregoing posterior approach, the bores inherently are angulated toward each other at about 5°–10° off true sagittal, and this provides the advantage of permitting the bore to be deeper before there is any danger of the drill bit emerging from the other side of the disc. Because that angle is quite small, the implanted prosthetic capsules act virtually as if their axes or elongated directions were positioned in the true sagittal direction.

Drilling of the facet joints can be avoided either by an anterior approach or by accessing the damaged disc posteriorly, medial to the facet joints. The latter approach involves the hazard of moving and thus possibly damaging the spinal nerves. Furthermore, this would require the bores in the disc to extend in the sagittal direction or slightly divergent from sagittal, so that the bores would need to be shorter than when drilling through facet windows. On the other hand a posterior approach medial to the facet joints may be feasible by a percutaneous technique in which the prosthetic disc capsules are moved into position with a minimum of disruption.

When the prosthetic capsule is connected to a remote chamber that is designed to be punctured by a hypodermic needle, the chamber should be placed to be easily approachable by a long needle under x-ray fluoroscopic control. If an implanted prosthetic disc capsule causes some remolding of the vertebral body bone, then the space height will decline, and reinflation may be used to restore the height, perhaps several times. Thixotropic gels of differing behavior may be required in various patients, and the ability to modify the gel after the prosthetic capsule has been implanted is permitted by a chamber which affords remote access to the bladder.

When the bladder is connected by tubing to a remote reservoir or chamber which has a needle-puncturable, self-sealing membrane, the bladder need not be filled with the thixotropic gel until after being inserted into the damaged disc. After the novel disc capsule has been inserted into a damaged disc, a hypodermic needle can be used to inject thixotropic gel into the chamber, thus forcing the gel through the tubing into the bladder and inflating the bladder. The bladder may thus be fully inflated immediately after its insertion, or it may be inflated a little at a time in order to adjust or slowly increase the height of the disc space. A slow restoration of the disc height would permit natural elastic recovery, whereas a sudden rise might further disrupt or tear the anulus of the disc. The chamber can also be used with a hypodermic needle to withdraw some of the gel if it is judged to be overinflated.

The chamber need not be needle-puncturable when it is separated into two compartments by a flexible, impermeable membrane. One of those compartments which communicates with the bladder and contains thixotropic gel while the other compartment may contain a hygroscopic material and is formed with a moisture-permeable wall. Moisture of the body causes a gradual swelling of the hygroscopic material, hence forcing a gradual flow of thixotropic material to inflate the bladder gradually.

In order to limit lateral bulging of the prosthetic disc capsule while in the disc space, strong, inert fibers may be woven into the outer layer to extend transversely through the bladder. These transverse fibers can be identical to the strong, inert fibers of the outer layer. When the prosthetic disc capsule is further inflated from a remote chamber, the transverse fibers will result primarily in an increase in the disc height.

The ends of the novel prosthetic disc capsules may be invaginated so that as internal pressure rises or falls with vertebral loading, the ends may invert or evert, exerting pressure against surrounding tissue. This means to permit flexibility of the prosthetic disc capsule does not require an elastic stretch and recoil of the structure.

To guard against the possibility that one of the prosthetic disc capsules may tend to work itself out, each of the capsules may be provided with circumferential flanges, like collars, formed to make the capsule easy to insert but more difficult to extract or to be spontaneously expelled.

To guard against the possibility of the capsule rotating in the space during insertion or after implantation, the capsule preferably is provided with longitudinal fins or vanes. Both such longitudinal vanes and circumferential flanges can be formed of strong, inert fibers which can be identical to the iibers of the outer layer.

The strong, inert fibers of the outer layer of the novel disc capsule and of other elements of the novel disc capsule can be made of carbon or a polymer, including either natural or synthetic polymers such as cold-drawn poly(ethylene terephthalate) polyester fibers. The bioresorbable material can be polylactic or polyglycolic acid or collagen (e.g., semi-synthetic), each of which normally becomes replaced by tissue ingrowth and thus becomes bonded to surrounding tissue. This replacement by living tissue assures the permanent flexibility of the implanted prosthesis. See U.S. Pat. No. 4,643,734 (Lin) which names additional useful bioresorbable materials.

The bioresorbable material may itself be fibrous and interwoven with the inert fibers. On the other hand, the outer layer, circumferential flanges, and longitudinal vanes can be woven together of inert fibers (either coated or uncoated with bioresorbable material) and then impregnated with bioresorable material.

After implantation, it is not necessary that there be an ingrowth of vertebral body bone into the outer layer of the prosthetic disc capsule so long as a close fibrous bond develops between the outer layer and the bone. The fibers of the outer layer preferably are woven to permit considerable pressure containment.

The bladder should be flexible but not necessarily elastic. Suitable materials for the bladder include oriented poly(ethylene terephthalate), high-density polypropylene, silicone rubber, and copolymers of silicone and carbonate.

When the novel prosthetic disc capsule includes a remote chamber, the bladder, chamber and connecting tubing preferably are formed of the same material, e.g., by blow molding. By making the bladder as well as the chamber of a self-sealing material, a needle can be used to pull the transverse fibers through the bladder and also to interweave them with fibers of the outer layer, preferably while simultaneously weaving the outer layer and its ridges and flanges. When the bladder is not self-sealing, it is desirable to form it in two halves which can be sealed together after transverse fibers have been put into place, followed by interweaving the ends of those transverse fibers with fibers of the outer layer.

The thixotropic gel may be a mixture of an inorganic oil (e.g., silicone or fluorocarbon) and a gelling agent such as fumed silica (preferably providing from approximately 3 to 10% by weight of the mixture and affording a Brookfield viscosity between 100 and 10,000 cps. at 6 rpm). The viscosity of the gel is selected to permit movement with normal rapidity during bending at the intervertebral space while restricting motion, especially during slow postural changes. A bulletin entitled "Cab-O-Sil Properties and Functions" from Cabot Corp. (dated 9/83) says at page 10 that "Cab-O-Sil" fumed silica has been authorized by F.D.A. for use in pharmaceutical products for internal and topical applications.

BRIEF DESCRIPTION OF THE DRAWING

In the drawing, all figures of which are schematic.

DESCRIPTION OF THE PREFERRED EMBODIMENT

Figure 1:
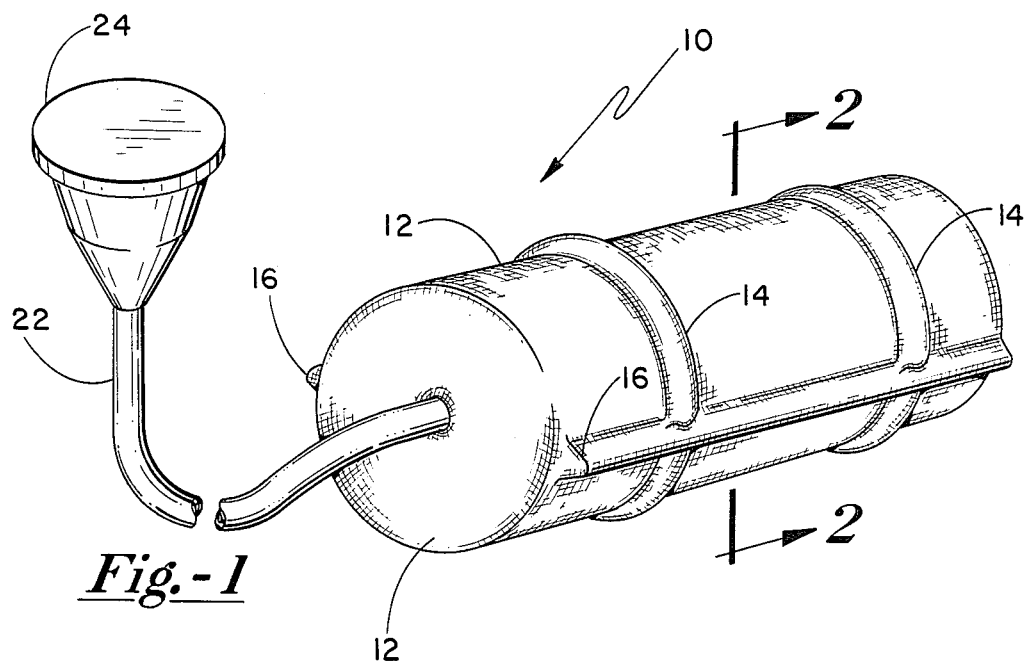
FIG. 1 is a perspective view of a preferred elongated prosthetic disc capsule of the invention with a remote chamber by which the capsule can be further inflated or deflated.

The elongated prosthetic disc capsule 10 shown in FIG. 1 has an outer layer 12 consisting of a network of strong, inert polymeric fibers interwoven with bioresorbable fibers which attract tissue ingrowth. Also interwoven with said fibers are strong, inert polymeric fibers arranged to form two circumferential bands or flanges 14 and longitudinal fins or vanes 16 that project from the external face of the outer layer 12.

Figure 2:
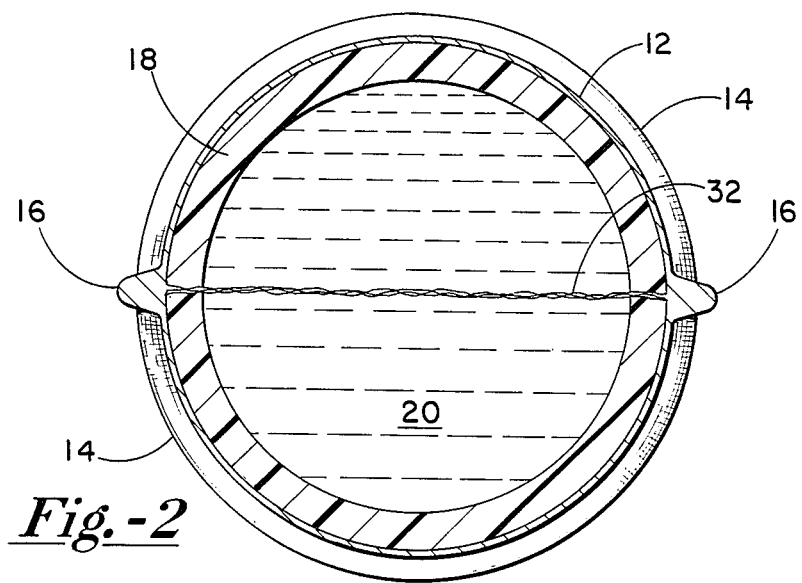
FIG. 2 is an enlarged central section along line 2—2 of FIG. 1.

The outer layer 12 surrounds a bladder 18 that contains a thixotropic gel 20 as seen in FIG. 2. A small tube 22 connects the bladder to a small remote chamber 24 consisting of a needle-puncturable, self-sealing membrane. After the prosthetic disc capsule 10 has been implanted into a human spine as shown in FIGS. 4 and 5, the tube 22 permits the chamber 24 to be positioned as in FIG. 4 so that thixotropic gel can be added to or drawn out of the chamber 24 by insertion of a hypodermic needle without penetrating into the spinal zone.

Figure 3:
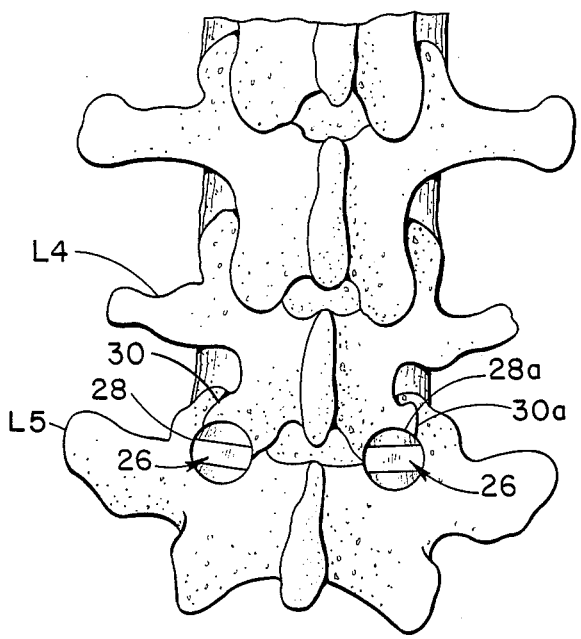
FIG. 3 is a posterior view of a human spine showing two windows that have been drilled through lower portions of facets to provide convenient access for implanting a pair of the prosthetic disc capsules of FIGS. 1 and 2 into a degenerated disc between the L4 and L5 vertebrae.

The zone of implantation is at a degenerated or herniated disc 26 between the L4 and L5 lumbar vertebrae. As seen in FIG. 3, windows 28 and 28a have been drilled into lower portions of the facets 30 and 30a. Using those windows, a pair of bores 31 and 31a have been drilled into the disc 26, with each bore near a lateral edge of the damaged disc 26 and angulated toward the other bore at about 10° to the sagittal direction. Also using those windows, the drilling debris and possibly other parts of the nucleus of the disc have been removed, after which the prosthetic disc capsule 10 and an identical prosthetic disc capsule 10a have been axially inserted into the bores 31 and 31a, respectively, without disturbing the spinal nerve.

Figure 4:
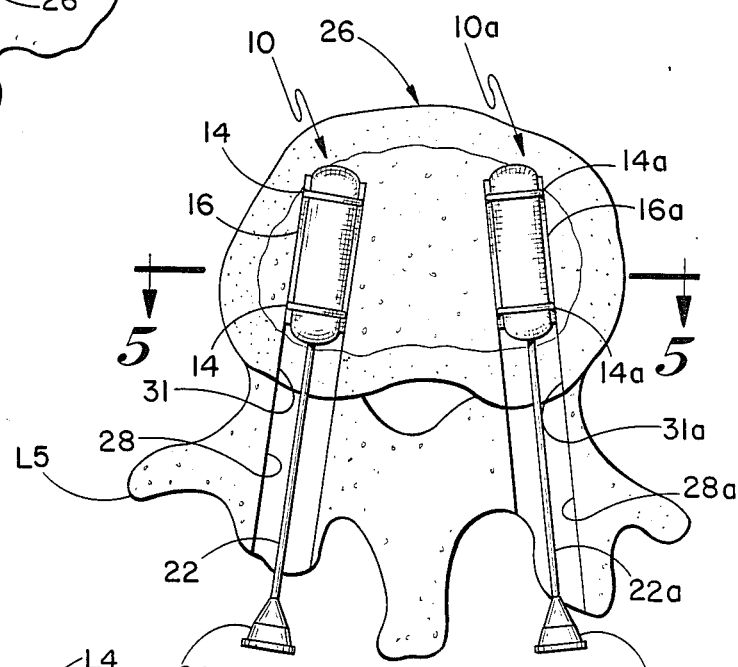
FIG. 4 is a transaxial view of the spine as prepared in FIG. 3 with the L4 vertebra not shown.
Figure 5:
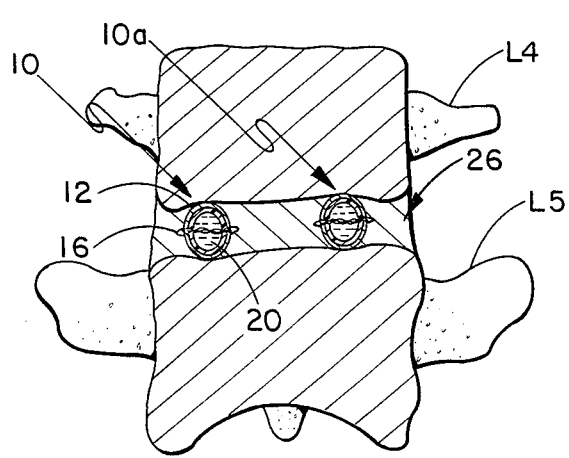
FIG. 5 is a section along line 5—5 of FIG. 4, reduced in size.

As seen in FIG. 4, the prosthetic disc capsules 10 and 10a have been inserted into the bores 31 and 31a and hence are positioned side-by-side and spaced apart with the elongated direction or axis of each of the capsules extending at an angle of about 10° to the sagittal direction. FIG. 5 shows that the prosthetic disc capsules 10 and 10a have restored the height of the space between the vertebrae L4 and L5 with a tightening of the anulus of the disc 26. This relieves pressure on the nerves that had been caused by a combination of collapse of the disc space and bulging of the weakened anulus.

Referring again to FIG. 2, a number of polymeric or other strong, inert fibers 32 extend transversely across the equator of the disc capsule 10 and are interwoven with the fibers of the outer layer 12. Because of these transverse fibers 32, the prosthetic disc capsule 10 resists becoming flattened by vertical pressures in the patient's spine, thus retaining the spacing between the lumbar vertebrae L4 and L5 between which it and the disc capsule 10a are implanted. The longitudinal vanes 16 and 16a serve to inhibit rotation of the prosthetic disc capsules, while the circumferential flanges 14 and 14a better anchor the disc capsules in the space between the vertebrae.

We claim:

1. An elongated cylindrical prosthetic intervertebral disc capsule adapted to be inserted in a sagittal direction within the nucleus of a damaged disc, said capsule having a diameter approximating the height of a human disc space and a length approximating the sagittal diameter of the nucleus of the disc, and said capsule comprising:

an outer layer of strong, inert fibers intermingled with a bioresorbable material which attracts tissue ingrowth, and a fluid-filled bladder, such that when two of these capsules are inserted side-by-side into the nucleus of the anulus of a damaged disc, each lying near one of the lateral edges of the disc and spaced from the other capsule, they will maintain both height and motion, including front-to-back bending, at the disc space, but will limit rotation.

2. A prosthetic disc capsule as defined in claim 1 wherein the fluid filling the bladder is a thixotropic gel having a viscosity and velocity-shear behavior imitating the natural rheology of intradiscal nuclear tissue.

3. A prosthetic disc capsule as defined in claim 2 wherein said thixotropic gel has a Brookfield viscosity between 100 and 10,000 cps. at 6 rpm.

4. A prosthetic disc capsule as defined in claim 1 having strong, inert fibers woven into the outer layer and extending transversely through the bladder to limit lateral bulging.

5. A prosthetic disc capsule as defined in claim 1 having external ridges or longitudinal vanes attached to the outside of the capsule to inhibit rotation of the capsule within the disc space.

6. A prosthetic disc capsule as defined in claim 1 wherein the ends of the capsule are invaginated.

7. A prosthetic disc capsule as defined in claim 1 wherein said bioresorbable material comprises fibers which are interwoven with said inert fibers.

8. A prosthetic disc capsule as defined in claim 1 wherein said bioresorbable material is coated on the inert fibers.

9. A prosthetic disc capsule as defined in claim 1 wherein said bioresorbable material is selected from polylactic acid, polyglycolic acid, and collagen.

10. A prosthetic disc capsule as defined in claim 1 and including a hollow tubing communicating with said bladder and an external chamber, and means for injecting or withdrawing fluid into or from the chamber.

11. A prosthetic disc capsule as defined in claim 10 wherein said chamber consists of a needle-puncturable, self-sealing membrane.

12. A surgical procedure involving the implantation of two prosthetic disc capsules side-by-side into the nucleus of the anulus of a damaged disc, said procedure comprising the steps of:

(1) jacking apart the vertebrae adjacent to a damaged disc, (2) forming a substantially sagittal bore in the damaged disc near each of its lateral edges and spaced from the other bore, and (3) inserting an elongated inflatable cylindrical disc capsule axially into each bore.

13. A surgical procedure as defined in claim 12 and involving the added step of opening a window to the damaged disc through a vertebral facet joint at each side of the spine, and step (2) involves drilling via each window a bore in the damaged disc.

14. A surgical procedure as defined in claim 13 wherein each of the bores drilled in the damaged disc in step (2) is angulated about 10° from the sagittal direction toward the other bore.

15. A surgical procedure as defined in claim 14 wherein step (4) involves inserting the prosthetic disc capsules through said windows.

16. A surgical procedure as defined in claim 12 wherein step (3) is followed by the step of inflating the prosthetic disc capsule.

* * * * *